(12) United States Patent
Kozak et al.

(10) Patent No.: US 6,605,638 B1
(45) Date of Patent: Aug. 12, 2003

(54) USE OF BRANCHED CHAIN FATTY ACIDS AND DERIVATIVES THEREOF FOR INHIBITION OF P-GLYCOPROTEIN

(75) Inventors: Alexander Kozak, Rehovot (IL); Roman Kamburg, Rishon LeZion (IL)

(73) Assignee: D-Pharm Limited, Rehovot (IL)

( * ) Notice: Subject to any disclaimer, the term of this patent is extended or adjusted under 35 U.S.C. 154(b) by 0 days.

(21) Appl. No.: 09/741,236

(22) Filed: Dec. 20, 2000

(51) Int. Cl.⁷ .............................................. A01N 37/00
(52) U.S. Cl. .................. 514/506; 514/557; 514/558; 514/740
(58) Field of Search .................... 424/422; 514/506, 514/557, 558, 740

(56) References Cited

U.S. PATENT DOCUMENTS

| | | |
|---|---|---|
| 5,591,715 A | 1/1997 | Coon et al. |
| 5,672,746 A | 9/1997 | Nau et al. |
| 5,681,812 A | 10/1997 | Coon et al. |
| 5,776,891 A | 7/1998 | Coon et al. |

FOREIGN PATENT DOCUMENTS

| | | | |
|---|---|---|---|
| JP | 63196283 | * | 8/1988 |

* cited by examiner

*Primary Examiner*—Alton N. Pryor
(74) *Attorney, Agent, or Firm*—Davidson, Davidson & Kappel, LLC

(57) ABSTRACT

The invention relates to the use of branched chain fatty acids (BFAs) and their derivatives for inhibition of the activity of P-glycoprotein (P-gp). In particular, the invention relates to the use of BFAs and their derivatives in the treatment of multi-drug resistant (MDR) tumors associated with increased activity of P-glycoprotein. The invention also relates to the use of the above-mentioned molecules for administration of biologically active molecules and diagnostic agents into cells associated with increased activity of P-gp, and for increasing accumulation of biologically active molecules and diagnostic agents in organs protected by biological barriers.

19 Claims, 6 Drawing Sheets

USE OF BRANCHED CHAIN FATTY ACIDS AND DERIVATIVES THEREOF FOR INHIBITION OF P-GLYCOPROTEIN

FIELD OF THE INVENTION

The present invention relates to the use of branched chain fatty acids (BFAs) and their derivatives for inhibition of the activity of P-glycoprotein. In particular, the invention relates to the use of BFAs and their derivatives in the treatment of multi-drug resistant (MDR) tumors associated with increased activity of P-glycoprotein and in methods for drug administration.

BACKGROUND OF THE INVENTION

A major problem in clinical pharmacology results from the phenomenon of multi-drug resistance (MDR) which endows mammalian cells with resistance to a broad spectrum of structurally unrelated cytotoxic drugs.

MDR is associated with the majority of human cancers, thus posing obstacles in the chemotherapeutic treatment with the consequence, in many cases, of poor prognosis. The multi-drug resistance may be inherent in a tumor cell, or may be acquired after an initial partial response to cytotoxic drugs.

One major type of MDR is related to overexpression of a plasma membrane glycoprotein, known as P-glycoprotein (P-gp). P-gp is a transmembrane protein of 170 kDa that is involved in ATP-dependent transport of molecules across the cytoplasmatic membrane. Elevated activity of P-gp leads to increased drug efflux and, hence, reduced intracellular accumulation of drugs. P-glycoprotein is also present in several normal human tissues as part of natural biological barriers protecting mammalian organs and tissues such as the blood brain barrier (BBB), the testes, eyes and gut-blood barriers, as well as in the epithelia of the bronchi and of genitourinary organs. Disorders or diseases of these organs and tissues encounter severe treatment problems due to insufficient drug penetration to the diseased site. The deficient drug bioavailability is further aggravated by the MDR phenomenon in cancers of these organs and tissues wherein tumor-blood barrier exists.

MDR severely limits the therapeutic efficacy of pharmacological compounds and can prevent treatment of malignant diseases. In certain cases, high systemic concentrations must be administered in order to achieve a therapeutic concentration of the active agent at the disease site. This elevated dosage results in increased side effects and toxicity.

A number of agents have been shown to potentiate the cytotoxic effects of certain drugs by increasing their intracellular concentration. These agents are termed chemosensitizers or MDR reversers, and include agents such as calcium channel antagonists, (e.g. verapamil), calmodulin inhibitors (e.g. prenylamine and trifluoroperazine), detergents and membrane-fluidizing agents (e.g Tween 80) and other compounds which reverse multi-drug resistance by yet unknown mechanisms (reviewed by Sharom, F. J. (1997) J. Membrane Biol. 160, 161–175). Many of the known chemosensitizing drugs suffer from severe drawbacks such as clinical toxicity frequently induced to healthy tissues.

Neurotrophic and antiproliferative compounds related to the antiepileptic drug valproate are disclosed in U.S. Pat. No. 5,672,746. According to said disclosure, the compounds per se are useful for promoting neuronal function and differentiation and for treating neoplastic diseases by arresting or retarding mitosis. However, the prior art does not disclose the compounds as having properties of P-gp-inhibitors hence being capable of enabling or increasing the penetration and/or accumulation of other biologically active molecules in cells associated with increased activity of P-glycoprotein.

It is still an unmet medical need to provide a pharmaceutical composition that enables effective penetration of therapeutic drugs or diagnostic reagents through biological barriers, particularly into multi-drug resistant cancerous cells, while producing minimal or no deleterious side effects to the healthy tissues.

SUMMARY OF THE INVENTION

It has been found, in accordance with the present invention, that some branched chain fatty acids and their derivatives (denoted herein as DP-BFAs) are capable of inhibiting the activity of P-glycoprotein (P-gp). These compounds are, thus, capable of reversing MDR and are useful in combination with antineoplastic drugs, when applied either separately or together, for the treatment of certain cancers.

The useful compounds according to the invention are of the general formula I:

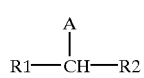

(I)

Wherein
  R1 is a saturated or unsaturated, substituted or unsubstituted hydrocarbon chain having from 1 to 10 carbon atoms;
  R2 is a saturated or unsaturated, substituted or unsubstituted hydrocarbon chain having from 5 to 30 carbon atoms;
  A is selected from the group consisting of C(O)O—R', C(O)NR'—R" and C(O)O⁻ Y⁺, wherein R' and R" are each independently selected from the group consisting of hydrogen and a lower alkyl group comprising 1–5 carbon atoms, and Y denotes any pharmaceutically acceptable counter-ion.

Accordingly, the invention provides, in one aspect, a pharmaceutical composition for inhibition of the activity of P-glycoprotein comprising an effective amount of said compound of the above-denoted general formula I together with a pharmaceutically acceptable carrier or excipient.

In a currently preferred embodiment, the compound of the general formula I is selected from the group consisting of:
  2-propylnonanoic acid,
  2-propyldodecanoic acid,
  2-propyltetradecanoic acid,
  2-propythexadecanoic acid,
  2-propyloctadecanoic acid,
  2-propyleicosanoic acid,
  2-heptylnonanoic acid,
  2-heptyldodecanoic acid,
  2-heptyhexadecanoic acid,
  2-decyldodecanoic acid,
  2-decylhexadecanoic acid,
  2-tetradecylhexadecanoic acid,
  2,3-propynyltetradecanoic acid,
  2,3-propynylhexadecanoic acid, 2-propylnonanoylamide,
2-propyldecanoylamide,
2-propyltetradecanoylamide,
2-propylhexadecanoylamide,
2-propyloctadecanoylamide, and
2-propyleicosanoylamide.

In another preferred embodiment, the useful pharmaceutical composition in accordance with the invention further comprises an anti-cancer drug. Said anti-cancer drugs may be selected from, but are not limited to, alkaloids (e.g. taxol, vinblastine, vindesine and vincristine), alkylating agents such as alkyl sulfonates, aziridines, ethylenimines, methylmelarnines, nitrogen mustards (e.g. cyclophosphamide) and nitrosoureas, antibiotics and analogs (e.g. aclacinomycin, actinomycin, anthramycin, daunorubicin and doxorubicin), antimetabolites such as folic acid analogs (e.g. raltitrexed), purine and pyrimidine analogs and platinum complexes (e.g. carboplatin, cisplatin, miboplatin and oxaliplatin).

The pharmaceutical compositions are useful in the treatment of tumors associated with increased activity of P-glycoprotein and tumors which are multi-drug resistant. Said tumors may be selected from, but not being limited to, carcinomas, sarcomas, leukemias, lymphomas, myelomas and gliomas.

The pharmaceutical compositions, according to the invention, are also useful for the administration of biologically active molecules and diagnostic agents into cells associated with increased activity of P-glycoprotein, and for increasing accumulation of biologically active molecules and diagnostic agents in organs protected by a biological barrier.

In a particular embodiment, the pharmaceutical compositions are useful for increasing drug absorption through biological barriers such as the gastrointestinal epithelium, epithelia of the nasal cavity, epithelia of the bronchi, renal epithelia etc.

In preferred embodiments, the pharmaceutical composition of the invention is suitable for oral or intravenous administration.

In another aspect, the invention provides the use of a compound of the general formula I:

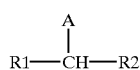
(I)

wherein
R1 is a saturated or unsaturated, substituted or unsubstituted hydrocarbon chain having from 1 to 10 carbon atoms;
R2 is a saturated or unsaturated, substituted or unsubstituted hydrocarbon chain having from 5 to 30 carbon atoms;
A is selected from the group consisting of C(O)O—R', C(O)NR'—R" and C(O)O⁻Y⁺, wherein R' and R" are each independently selected from the group consisting of hydrogen and a lower alkyl group comprising 1–5 carbon atoms, and Y denotes any pharmaceutically acceptable counter-ion, for the preparation of a medicament for inhibition of the activity of P-glycoprotein.

In yet another aspect, the invention provides a method for inhibiting the activity of P-glycoprotein comprising contacting cells having P-glycoprotein with an effective amount of a compound of the general formula I.

In a particular embodiment, a method is provided for treatment of a tumor associated with increased activity of P-glycoprotein, said method comprises administering to a patient in need thereof an effective amount of a compound of the general formula I as defined above, in combination with an anti-cancer drug. Preferably, the compound of the general formula I is intravenously or orally administered.

In a particularly preferred embodiment, the method is for the treatment of multi-drug resistant tumors.

In other embodiments of the invention, methods are provided for administration of diagnostic agents and/or biologically active molecules into cells associated with increased activity of P-glycoprotein. Said methods comprise contacting cells associated with increased activity of P-glycoprotein with a diagnostic agent and/or a biologically active molecule in the presence of an effective amount of a compound of the general formula I as defined above, thus enabling or increasing the penetration and/or accumulation of the diagnostic agent and/or biologically active molecule in the cells.

In yet other embodiments of the invention, methods are provided for increasing accumulation of a diagnostic agent and/or biologically active molecule in an organ protected by a biological barrier comprising administering to an individual said diagnostic agent and/or biologically active molecule in combination with an effective amount of a compound of the general formula I as defined above, thus increasing accumulation of the diagnostic agent and/or biologically active molecule in the organ protected by a biological barrier.

In still another embodiment of the invention, a method is provided for increasing bioavailability of a drug comprising administering to an individual said drug in combination with an effective amount of a compound of the general formula I.

Further objects of the present invention will become apparent to those skilled in the art upon further review of the following disclosure, including the detailed descriptions of specific embodiments of the invention.

DETAILED DESCRIPTION OF THE INVENTION

Figure 1:
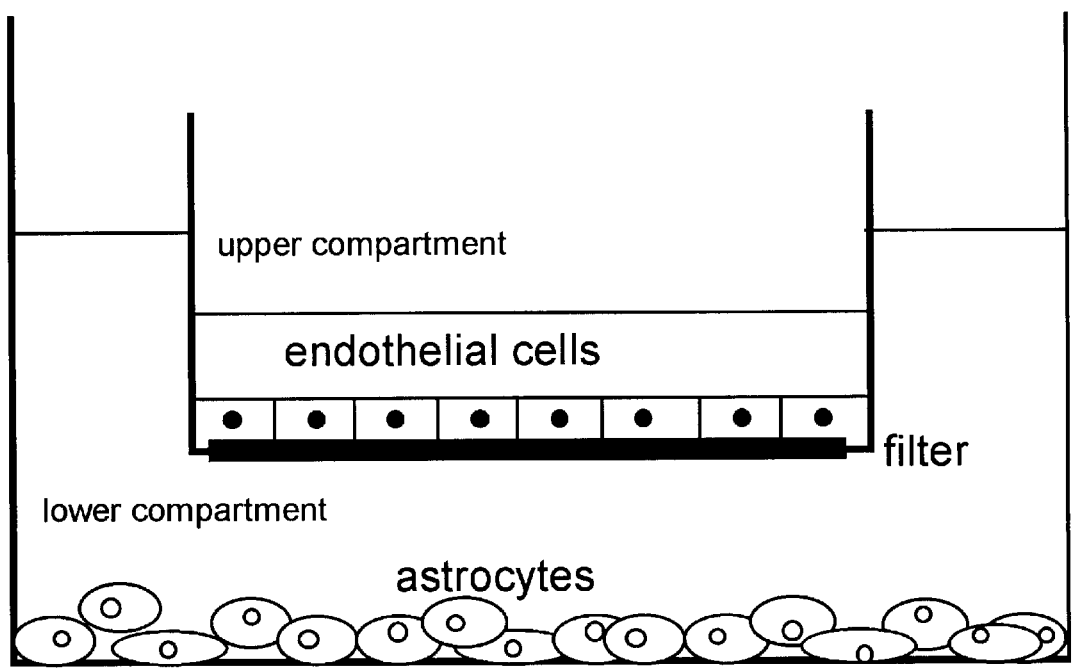
FIG. 1 depicts a scheme of the co-culture used for the in vitro model system of BBB and P-glycoprotein activity.

It is now disclosed, for the first time, that certain branched chain fatty acids and derivatives thereof, at concentrations as low as about 1 μg/ml, are capable of inhibiting the activity of P-glycoprotein (P-gp).

The useful compounds in accordance with the invention are of the general formula I

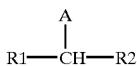

(I)

wherein
- R1 is a saturated or unsaturated, substituted or unsubstituted hydrocarbon chain having from 1 to 10 carbon atoms;
- R2 is a saturated or unsaturated, substituted or unsubstituted hydrocarbon chain having from 5 to 30 carbon atoms;
- A is selected from the group consisting of C(O)O—R', C(O)NR'—R" and C(O)O$^-$Y$^+$, wherein R' and R" are each independently selected from the group consisting of hydrogen and a lower alkyl group comprising 1–5 carbon atoms, and Y denotes any pharmaceutically acceptable counter-ion.

The pharmaceutically acceptable counter-ion Y may be selected, but is not limited to, inorganic cations such as ammonium, calcium, magnesium, potassium, sodium, iron, zinc and the like, and organic bases including primary, secondary, tertiary and quarternary organic ammonium cations.

The salts, esters and amides of the compound of the general formula I may be formed by means known in the art, and may be used to modify the pharmaceutical properties of the branched chain fatty acid insofar as stability, solubility etc., are concerned.

Throughout the specification and claims the following abbreviations and terms will be used:
BBB—stands for blood brain barrier; BFA—stands for branched chain fatty acid; DP-BFA—denotes branched chain fatty acids and derivatives thereof of the general formula I as defined above. Specific DP-BFAs are referred to by their particular R1 and R2 that represent the number of carbon atoms in the branched alkyl chains of the molecule, e.g. DP-3,10, DP-7,7 etc.; MDR—stands for multi-drug resistance; P-gp—stands for P-glycoprotein.

The term "bioactive substance" refers to therapeutic and other biologically active molecules capable of modifying cellular functions, as well as to substances for diagnostic purposes.

The term "effective amount" of a compound of the general formula I refers to that amount of a given branched chain fatty acid or a derivative thereof in accordance with the invention, which is capable of antagonizing and/or inhibiting the P-glycoprotein activity.

The term "tumor" as used herein refers to any malignant cell growth which may be manifested as primary tumors, metastases, solid or diffuse tumors or individual cancerous cells.

The use of the compounds of the general formula I in accordance with the invention is beneficial in overcoming low efficacies of therapeutic drugs, in particular in the case of malignant diseases or tumors associated with increase activity of P-gp that prevents efficient penetration of multiple drugs into the cancerous cell.

In one particular embodiment, the compositions of the invention are useful in the treatment of diseases and tumors of the brain, which are protected by a layer of endothelial cells collectively known as the blood-brain barrier (BBB). The same applies to other organs and tissues in mammals that are protected by such blood-related barriers, such as the testes, eye and the other biological barriers such as those of the gastrointestinal and genitourinary organs (e.g. prostate gland, kidney etc.). Chemotherapy treatment of these organs and tissues encounters severe limitations due to the poor accessibility of drugs to the diseased site. MDR that further diminishes drug penetration imposes an additional complication, hence further impairing the success rate of the treatment.

Co-treatment of tumors associated with increased activity of P-gp with chemotherapy in combination with a pharmaceutical composition in accordance with the invention is advantageous over treatment with chemotherapy alone. In accordance with the invention, the anti-cancer drug(s) may be included in the same pharmaceutical composition of the compound of the general formula I, or may be administered in a separate composition. Preferably both active agents, i.e. the compound of the general formula I and the anti-cancer drug(s) are administered simultaneously or within a short period of time from one another.

Any anti-cancer drug that is suitable for use in chemotherapy procedures may be applied in combination with the compound of the general formula I. Suitable anti-cancer drugs may include, but are not limited to, alkaloids (e.g. taxol, vinblastine, vindesine and vincristine), alkylating agents such as alkyl sulfonates, aziridines, ethylenimines, methylmelamines, nitrogen mustards (e.g. cyclophosphamide) and nitrosoureas, antibiotics and analogs (e.g. aclacinomycin, actinomycin, anthramycin, daunorubicin and doxorubicin), antimetabolites such as folic acid analogs (e.g. raltitrexed), purine and pyrimidine analogs and platinum complexes (e.g. carboplatin, cisplatin, miboplatin and oxaliplatin).

It will be readily apparent to those of ordinary skill in the art that a large number of other anti-cancer drugs may be used as antineoplastic agents, therefore are included within the scope of the invention as compounds useful in pharmaceutical compositions or methods of treatment in accordance with the invention.

In another aspect, the invention provides a method for inhibiting the activity of P-glycoprotein comprising contacting cells having P-glycoprotein with an effective amount of a compound of the general formula I.

In a preferred embodiment of the invention this method is applied for the treatment of tumors associated with increased activity of P-glycoprotein, which method comprising administering to a patient in need thereof an effective amount of a compound of the general formula I as defined above, in combination with an anti-cancer drug.

In a preferred embodiment the effective amount of the compound of the general formula I is from about 1 μg/ml to about 100 μg/ml. These concentrations of BFA are sufficient for inhibiting the P-glycoprotein activity, while inducing a minimal opening of the tight junctions of the BBB, if at all. Hence, said preferred effective amount lacks general toxicity and deleterious side effects in vivo. The preferred effective amount at the target sites may be achieved by administering a pharmaceutical composition comprising a compound of the general formula I in the range of from about 0.01 to about 1 mg/kg body weight.

The therapeutically effective amounts of the active agents, i.e. the compound of the general formula I and the anti-cancer drug(s), and their combinations capable of inducing a therapeutic alteration in the physiological state of the treated patient, can be empirically determined by medical personnel skilled in the art.

The dose range and the regimen employed will be dependent on the route of administration, the age, sex, health and weight of the recipient and on the potency of the particular BFA and the relevant anti-cancer drug administered. The skilled artisan will be able to adjust the BFA compositions and dosage in order to obtain the desired duration and the degree of action.

The pharmaceutical compositions may be in a liquid, aerosol or solid dosage form, and may be formulated into any suitable formulation including, but is not limited to, solutions, suspensions, micelles, emulsions, microemulsions, aerosols, ointments, gels, suppositories, capsules, tablets, and the like, as will be required for the appropriate route of administration.

Any suitable route of administration is encompassed by the invention including, but not being limited to, oral, intravenous, intramuscular, subcutaneous, inhalation, intranasal, topical, rectal or other known routes. In preferred embodiments, the pharmaceutical composition of the invention is intravenously or orally administered.

The pharmaceutical compositions in accordance with the invention are useful in the treatment of any pathological condition associated with increased activity of P-glycoproteins. In particular the pharmaceutical compositions are useful for the treatment of multi-drug resistant tumors. Said tumors include, but are not limited to, carcinomas (e.g. small cell lung cancer, colon, kidney and breast carcinomas), sarcomas (e.g osteosarcoma), leukemias, lymphomas, myelomas (e.g. multiple myeloma), gliomas and pediatric cancers.

In addition, the use of the compositions of the invention is beneficial in improving the administration of bioactive substances into cells and organs characterized by elevated activity of P-glycoprotein. Thus, according to other embodiments of the invention, methods are provided for administration of diagnostic agents and/or biologically active molecules into cells associated with increased activity of P-glycoprotein. The methods involve contacting said cells with the bioactive substance(s) in the presence of an effective amount of a branched chain fatty acid or a derivative thereof in accordance with the invention, thus enabling or increasing the penetration and/or accumulation of the bioactive substance(s) in the treated cells.

Another use of the compositions in accordance with the invention is in methods for increasing accumulation of beneficial bioactive substances in an organ protected by a biological barrier comprising administering to an individual said bioactive substance in combination with an effective amount of a branched chain fatty acid or a derivative thereof according to the invention.

It should be clarified that within the scope of the bioactive substances as used herein are included therapeutic and other biologically active molecules capable of modifying cellular functions, as well as substances for diagnostic purposes such as, for example, various contrasting agents used for imaging of tumors.

In another embodiment of the invention, a method is provided for increasing bioavailability of drugs. Numerous factors affect bioavailability of drugs, including the route of drug administration and its absorption and distribution in the body tissues and organs. Drug bioavailability is reduced by the activity of P-glycoprotien that is expressed not only in tumor cells, but also in several normal tissues such as in the apical surface of many epithelial cells and in the endothelial cells of the blood-brain barrier. For example, P-gp action as an efflux pump may limit the uptake of orally administered compounds from the gastrointestinal tract. In addition, blood-tissue barriers contribute to drug exclusion from the protected organs, and the presence of P-gp in excretory tissues such as the liver, intestine and kidney may account for active excretion of the drug.

By administrating a drug in combination with an effective amount of a branched chain fatty acid or a derivative thereof in accordance with the invention, inhibition of P-gp activity is achieved. This results in increasing drug bioavailability manifested in terms of increased intracellular accumulation of the drug and/or its longer retention time at the target site.

EXAMPLES

I. Chemical Examples

Example 1

Synthesis of 2-Alkyl Fatty Acids (BFA)

The synthesis of 2-alkyl fatty acids also known as dialkyl acetic acids is based on well-known principals of organic chemistry and is generically accomplished by a four-stage procedure.

A general synthesis protocol comprises the following stages:

The first stage is alkylation of diethyl ester of malonic acid.

The second stage is alkylation of diethyl ester of alkyl-malonate.

The third stage is hydrolysis of diethyl ester of dialkyl-malonic acid.

The final product is prepared by decarboxylation of the corresponding dialkylmalonic acid.

This synthesis procedure is exemplified hereinbelow in the detailed description of the synthesis of 2-propylhexadecanoic acid. The procedure for preparation of other 2-alkyl fatty acids is analogous to the synthesis of 2-propyl hexadecanoic acid. It should also be clear that the synthesis is not limited to saturated compounds of the general formula I, but rather applies to compounds of the general formula I wherein R1, R2 or both are either saturated or unsaturated, substituted or unsubstituted hydrocarbon chain.

Stage I. Synthesis of diethylpropylmalonate.

This stage comprises two steps: i) metallation of diethyl ester of malonic acid by sodium hydride, followed by ii) alkylation of the sodium diethyl ester malonate.

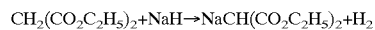

$$CH_2(CO_2C_2H_5)_2 + NaH \rightarrow NaCH(CO_2C_2H_5)_2 + H_2 \qquad \text{i)}$$

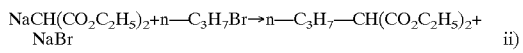

Sodium hydride (8.25 gr., 0.344 mol) is introduced, under an inert atmosphere of argon, into a two-neck flask (1 L), equipped with a magnetic stirrer and a reverse condenser (water cooling). Anhydrous tetrahydrofuran (THF, 100 ml), freshly distilled under LiAlH4, is also introduced into the flask under argon. A solution of diethyl malonate (49.92 gr., 0.312 mol) in THF (150 ml) is added drop-wise to the mixture of NaH with THF while being stirred by a magnetic stirrer. Stirring of the mixture is continued until hydrogen bubbles evolve from the mixture. A solution of propyl bromide (42.31 gr., 0.344 mol) in THF (50 ml) is then added drop-wise. In order to complete the reaction the mixture is heated at 50–60° C. for 5 hours. The mixture is then cooled to room temperature and the unreacted sodium hydride is decomposed by ethanol (50 ml). The precipitate is filtered and the resulting solution is evaporated under vacuum (about 25 mm Hg). The residue is dissolved in petroleum ether (200 ml) and the solution is washed with water (3×100 ml) in a separated funnel. The organic phase is dried with $MgSO_4$ and the petroleum ether is distilled under vacuum. The resulting oil is purified by silica gel chromatography using a gradient of petroleum ether/ether from 100/0% to 94/6%. Yield of the diethyl propylmalonate is 50.75 gr (0.250 mol).

TLC analysis: Silica gel 60 $F_{254}$ on aluminum sheet. Eluent is a mixture of petroleum ether with diethyl ether (9:1 v/v). The chromatogram is sprayed with an indicator and then charred at 150° C. The composition of the indicator spray is: 4-methoxybenzaldehyde (10 ml), ethanol (200 ml), 98% $H_2SO_4$ (10 ml) and glacial acetic acid (2 ml). Results: one spot. $R_f$ 0.45.

Stage II. Synthesis of diethylpropyltetradecylmalonate.

This stage comprises two steps: i) metallation of alkyl diethyl ester malonate by sodium hydride, followed by ii) alkylation of the sodium alkyl diethyl ester malonate.

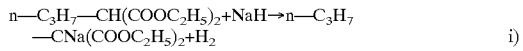
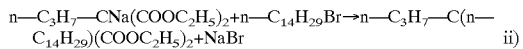

Sodium hydride (6.6 g., 0.275 mol) is introduced, under an inert atmosphere of argon, into a round-bottom double-neck flask (1 L), equipped with magnetic stirrer and a reverse condenser (water cooling). Anhydrous THF (150 ml) is added into the flask, also under argon. The drop funnel is joined to the flask and the solution of diethyl propylmalonate (50.75 g., 0.250 mol) in 150 ml of THF is added drop-wise to the mixture of NaH with THF. The mixture is stirred with a magnetic stirrer. When the emission of hydrogen bubbles from the reaction mixture stops, the drop funnel with the solution of tetradecylbromide (69.0 g., 0.250 mol) in 150 ml of THF is added to the flask and the solution is introduced drop-wise into the reaction mixture. The reaction mixture is heated for 5 hours at 50–60° C. The flask is then cooled to room temperature and the unreacted sodium hydride is decomposed using ethanol (50 ml). The resulting solution is evaporated under vacuum (about 40 mm Hg). About 500 ml of petroleum ether is added to the residue and the solution is washed with water (3×150 ml). The organic solution is dried with $MgSO_4$ and the solvent is evaporated under vacuum (30 mm Hg). The resulting crude product is purified by column chromatography. For purification of 1 gr. Crude product, 40 g. of silica gel 60 (70–230 mesh) were used. The eluent is a gradient of petroleum ether/ether from 100/0% to 94/6%. The yield of diethyl propyltetradecylmalonate is 50% (45 g.).

TLC analysis: Silica gel 60 $F_{254}$ on an aluminum sheet. Eluent is a mixture of petroleum ether with diethyl ether (9:1 v/v). ). The chromatogram is sprayed with an indicator (same composition as in stage I) and then burned at 350° C. Results: one spot. $R_f$ 0.65.

Stage III. Hydrolysis of diethyl propyltetradecyl-malonate.

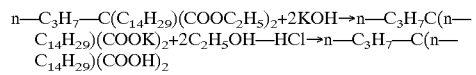

Diethyl propyltetradecylmalonate (45 g., 0.113 mol), potassium hydroxide (38 g., 0.678 mol), water (40 ml) and ethanol (80 ml) are introduced into a round-bottom single-neck flask (250 ml), equipped with a magnetic stirrer and a reverse condenser. The reaction mixture is heated in an oil bath for 4 hours at 90° C. The reaction is then cooled to room temperature and the mixture is transferred into a separated funnel. The unreacted diethyl propyltetradecylmalonate is extracted with petroleum ether (3×100 ml). The remaining water solution is cooled with ice and acidified by concentrated hydrochloric acid to pH 1–2. The resulting propyltetradecylmalonic acid is extracted by chloroform (3×100 ml) and is dried by $MgSO_4$. The chloroform is evaporated under vacuum (25 mm Hg). Yield of propyltetradecylmalonic acid is 90% (36 g.)

TLC analysis: Silica gel 60 $F_{254}$ on aluminum sheet. Eluent is mixture of chloroform with methanol (95:5 v/v). The chromatogram is sprayed with an indicator spray (same composition as in stage I) and charred at 150° C. Results: one spot. $R_f$ 0.05.

Stage IV. Decarboxylation of propyltetradecyl-malonic acid.

Propyltetradecylmalonic acid (36.0 g., 0.105 mol) is introduced into a single-neck round-bottom flask (150 ml) and is heated in an oil bath at 150–160° C. until $CO_2$ bubbles are no longer visible. For completion of the reaction, the flask is joined to vacuum (40 mm Hg) and heated at 120° C. for 1 hour. The resulting 2-propyl hexadecanoic acid is purified by column chromatography. For purification of 1 gr. crude product, 40 g. of silica gel 60 (70–230 mesh) were used. The eluent is a mixture of chloroform with methanol (97:3 v/v). After the chromatographic purification, a white solid product. m.p. 41.2° C., was obtained.

TLC analysis: Silica gel 60 $F_{254}$ on aluminum sheet. Eluent is a mixture of chloroform with methanol (95:5 v/v). The chromatograni is sprayed with an indicator spray (same composition as in stage I) and charred at 150° C. Results: one spot. $R_f$ 0.85.

Elemental analyses: $C_{19}H_{38}O_2$. Calculated: C 76.51%, H 12.75%. Found: C 76.19%, H 13.55%. $^1H$ NMR ($CDCL_3$), δ(Ppm): 0.85–0.97 (m. 6H), 1.30 (broad s. 26H), 1.33–1.50 (m.2H), 1.59–1.65 (m. 2H) and 2.36 (m. 1H).

Example 2

Synthesis of Amide Analogs of 2-Alkyl Fatty Acids

The synthesis of amide analogs of 2-alkyl fatty acids is a two-step procedure. The chloride derivative of the branched chain fatty acid is prepared at the first stage, followed by addition of the amine at the second stage. This synthesis procedure is exemplified below in the synthesis of 2-propyloctadecanoylamide. Amides of other 2-alkyl fatty acids are prepared according to an analogous procedure.

Overall, the synthesis can be described according to the following pathway:

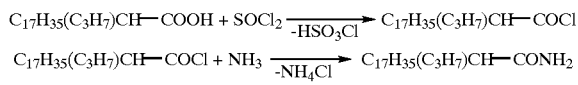

2-Propyloctadecanoic acid (200 mg, 0.61 mmol) was introduced into a single neck round-bottom flask, equipped with a magnetic stirrer and a reverse condenser. Three milliliters of $SO_2Cl_2$ was also placed in the flask. The reaction mixture was brought to reflux and left for one hour. The reaction mixture was then evaporated. The dry benzene (5 ml) was added to the residue and then evaporated. This procedure was repeated twice. The resultant residue was dissolved in 5 ml of dry tetrahydrofuran and then 0.2 ml of 0.5 M ammonia in dioxane was added to this solution. The suspension thus obtained was stirred with the magnetic stirrer for one hour and then evaporated. Petroleum ether was added to the residue and the mixture was stirred. The obtained solid was filtered, and then washed by water and petroleum ether twice. The precipitate was dried under vacuum (10 mm Hg) for three hours at room temperature. The product was a white powder. The yield was 80%.
TLC analysis: Silica gel 60 $F_{254}$ on aluminum sheet. Eluent was a mixture of petroleum ether with diethyl ether (3:7, v/v). Indicator was a spray of 4-methoxybenzaldehyde (10 ml), abs. ethanol (200 ml), 98% sulfuric acid (10 ml), glacial acetic acid (2 ml). The chromatogram was sprayed with this indicator, dried and then charred at 100–150 °C. One spot was observed. $R_f$=0.2.
Elemental analyses: $C_{23}H_{47}NO$. Calculated: C 78.19%, H 13.31%, N 3.97%. Found: C 78.09%, H 13.11%, N 3.77%.
$^1H$ NMR. ($CDCL_3$), δ(ppm): 0.84–0.93 (m, 6H), 1.24–1.41 (m, 34H), 1.52–1.60 (broad s, 4H), 2.06–2.15 (m,1H) and 5.30–5.36 (d, 2H).

II. DP-BFA Effect on P-Glycoprotein

Example 3 in vitro Model System for Permeability Studies

The effect of branched chain fatty acids on P-glycoprotein (P-gp) was evaluated in permeability studies carried out on a monolayer of endothelial cells in an in vitro model system of the blood-brain barrier (BBB).

It was previously shown by Fenart et al. (Fenart L., Buée-Scherrer V., Descamps L., Duhem C., Poullain M.-G., Cecchelli R. and Dehouck M.-P. (1998) Pharm. Res. 15(7): 993–1000) that P-glycoprotein is expressed in cultured endothelial cells. It was also shown by the same authors (Fenart et al. supra) that an increase in the vincristine transport across the endothelial cell monolayers was obtained using S9788 or verapamil as reversing agents.

The BBB model system is thus appropriate for studying the effect of BFA on endothelial permeability of the P-glycoprotein dependent drug, vincristine.
The Experimental System: in vitro Model System of the BBB The in vitro model system was developed for studying brain capillary functions. A process of co-culture was used that closely mimics the "in vivo" situation by culturing brain capillary endothelial cells on one side of a filter and astrocytes on the other (Dehouck, et al. (1992) J. Neurochemistry 58:1790–1797).

A scheme of the co-culture is shown in FIG. 1. Endothelial cells are cultured in the upper compartment on the filter and astrocytes in the lower compartment on the plastic of the Petri dish.

Under these conditions, endothelial cells retain all the endothelial markers (factor VIII—related antigen, non-thrombogenic surface, production of prostacyclin, angiotensin converting enzyme activity) and the characteristics of the blood-brain barrier (presence of tight junctions, paucity of pinocytotic vesicles, monoamine oxidase activity, y-glutamyltranspeptidase activity).
Initiation and Culture of Bovine Brain Capillary Endothelial Cells Bovine brain capillary endothelial cells were isolated and characterized as described by Méresse et al. (Méresse et al. (1989) J. Neurochem. 53, 1363–1371). In brief, after isolation by mechanical homogenization from one hemisphere of bovine brain, microvessels were seeded onto dishes coated with an extracellular matrix secreted by bovine corneal endothelial cells. Five days after seeding, the first endothelial cells migrated out from the capillaries and began to form microcolonies. When the colonies were sufficiently large, the five largest islands were trypsinized and seeded onto 35-mm-diameter gelatin-coated dishes (one clone per dish) in the presence of Dulbecco's modified Eagle's medium (DMEM) supplemented with 10% calf serum and 10% horse serum, 2 mM glutamine, 50 µg/ml of gentamicin and bovine fibroblast growth factor (1 ng/ml added every other day). Endothelial cells from one 35-mm-diameter dish were harvested at confluence and seeded onto 60-mm-diameter gelatin-coated dishes. After 6–8 days, confluent cells were subcultured at the split ratio of 1:20. Cells at the third passage were stored in liquid nitrogen.
Culture of Rat Astrocytes Primary cultures of astrocytes were made from newborn rat cerebral cortex. After the meninges had been cleaned off, the brain tissue was forced gently through a nylon sieve. DMEM supplemented with 10% fetal calf serum, 2 mM glutamine, and 50 µg/ml of gentamicin was used for the dissociation of cerebral tissue and development of astrocytes.
Preparation of Filters Culture plate inserts (Millicell-PC 0.4 µm; 30-mm diam; Millipore Corp., Milford, Mass.) were coated on the upperside with rat-tail collagen prepared by modification of the method of Bornstein (Bornstein, M. B (1958) Lab. Invest. 7, 134–139).
Co-culture of Bovine Brain Capillary Endothelial Cells and Astrocytes The astrocytes are plated at a concentration of $1.25 \times 10^5$ cells/ml on plastic in six-well plates. The medium is changed twice a week. Three weeks after seeding, cultures of astrocytes become stabilized. Then, endothelial cells frozen at passage 3, are recultured on a 60-mm-diameter gelatin-coated dish.

Confluent cells are trypsinized and plated on the upper side of the filters at a concentration of $4 \times 10^5$ cells. The medium used for the co-culture is DMEM supplemented with 10% calf serum and 10% horse serum, 2 mM glutamine, 50 µg/ml of gentamicin, and 1 ng/ml of bovine fibroblast growth factor added every other day. Under these conditions, endothelial cells form a confluent monolayer in 12 days.
Materials Ringer Hepes buffer solution: pH 7.4: NaCl 150 mM, KCl 5.2 mM, $CaCl_2$ 2.2 mM, $MgCl_2 6H_2O$ 0.2 mM, $NaHCO_3$ 6 mM, Hepes 5 mM, Glucose 2.8 mM.

Vincristine—[γ-$^3$H]Vincristine sulphate in methanol solution, 11.4 mCi/mg, MW=924 (Amersham). Stock solution of vincristine was added directly to the Ringer Hepes (upper compartment) with a dilution of 1:475.

Verapamil—verapamil hydrochloride, $C_{27}H_{38}N_2O_4 \cdot HCl$, MW=491.1 (SIGMA). The compound was dissolved in sterile water to obtain 2.5 mM. Stock solution of verapamil was added directly to the Ringer Hepes (upper compartment) with a dilution of 1:100 to yield final concentration 25 µM.

$[^{14}C]$-Sucrose—MW=342. 0.05 µCi/ml (Amersham).

Calculation of Clearance and Permeability Coefficient

To obtain a concentration-dependent transport parameter, the clearance principle was used. For each time, the increment in cleared volume between successive sampling events was calculated by dividing the amount of transported solute by the donor chamber concentration. The total volume cleared at each point was calculated by summing the incremental cleared volumes up to the given time point:

$$\text{Clearance } (\mu l) = \frac{[C]_A \times V_A}{[C]_L}$$

where $[C]_L$ is the initial luminal tracer concentration, $[C]_A$ the abluminal tracer concentration, and VA the volume of the abluminal chamber. During the 60-min experiment, the clearance volume increased linearly with time. The average volume cleared was plotted versus time, and the slope was estimated by linear regression analysis to give the mean and the SE to the estimate. The slope of the clearance curves for the co-culture was denoted $PS_t$, where PS is the permeability x surface area product (in microliters per minute). The slope of the clearance curve for the control filter was denoted $PS_f$.

The PS value for the endothelial monolayer $(PS_e)$ was calculated from $$\frac{1}{PSe} = \frac{1}{PSt} - \frac{1}{PSf}$$

The $PS_e$ values were divided by the surface area of the Millicell-PC (4.2 cm²) to generate the endothelial permeability coefficient ($P_e$, in centimeters per minute).

The permeability coefficient cannot be calculated when the clearance volume does not increase linearly with time. In that case, the results are presented as clearance (µl) in function of time (min.) and as percentage of the drug transported across the endothelial cell monolayers, defined by the ratio abluminal quantity/luminal quantity at a specific time point.

Example 4

Effect of Concentrations Over 0.1 mg/ml of DP-BFA on P-Glycoprotein

The permeability of the monolayer of endothelial cells was studied in the in vitro model system of the BBB described above in Example 3. The is clearance and accumulation of the P-gp-dependent drug, $[^3H]$-vincristine (50 nM), was investigated in the absence and presence of 0.08, 0.16 or 0.32 mg/ml of the compound 2-propylhexadecanoic acid (denoted herein as DP-3,14). As a control served $[^3H]$-vincristine (50 nM) incubated with filters without endothelial cells. $[^{14}C]$-sucrose was added to each incubation well (as a paracellular tracer) in order to follow the integrity of the endothelial cell monolayers during the experiments.

The results obtained with DP-3,14 were compared to the effect of verapamil that is a known reversing agent and one of the most frequently used P-gp inhibitors.

On the day of the experiments, the medium was aspirated. Ringer Hepes (2500 µl) was added to the lower compartment of the six-well plate. Ringer Hepes (1500 µl) containing 50 nM of $[^3H]$-vincristine and 0.05 µCi/ml of $[^{14}C]$ sucrose±verapamil or DP-3,14 was placed in the upper compartment. Triplicate co-cultures were assayed for each experiment. At 10, 20, 30, 45 and 60 min after addition of the compound, the insert was transferred to another well of the six-well to minimise the possible passage of substances from the lower to the upper compartment.

Incubations were performed on a rocking platform at 37° C. An aliquot from each well was placed in a scintillation vial, and the radioactivity was determined.

To obtain a concentration-dependent transport parameter, the clearance principle was used.

After 60 min transport experiment, cells were washed twice with ice-cold buffered Ringer solution and scraped gently to measure cell uptake. The radioactivity in the cells was determined. These steps were performed quickly in order to prevent any drug efflux.

Figure 2:
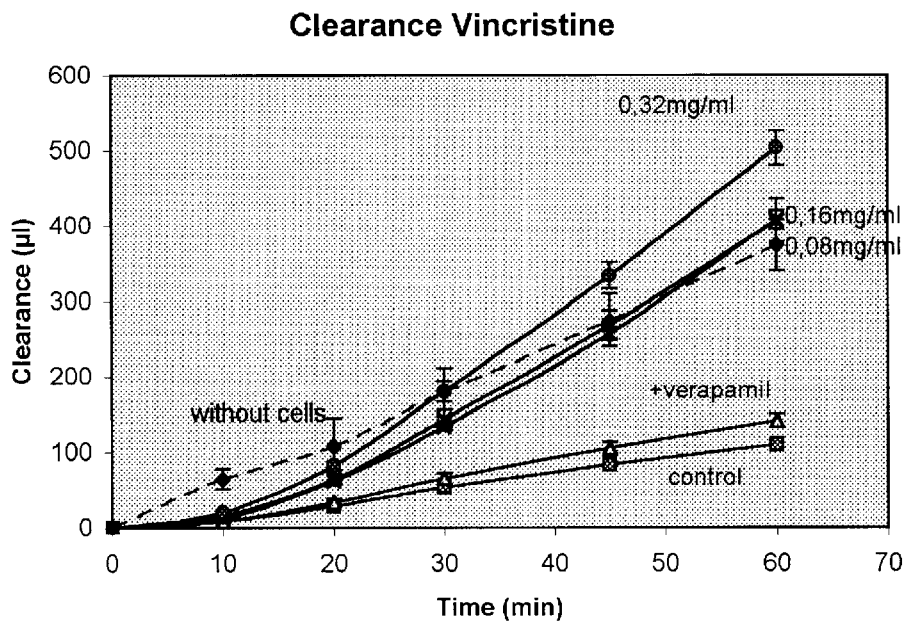
FIG. 2 depicts clearance of [$^3$H]-vincristine in the in vitro model system of BBB, as a function of incubation time with either verapamil, 0.08 mg/ml, 0.16 mg/ml or 0.32 mg/ml DP-BFA. As controls serve the clearances of vincristine through filters with and without endothelial cells in the presence of [$^3$H]-vincristine+$^{14}$C-sucrose only (marked as "control" and "without cells", respectively).
Figure 3:
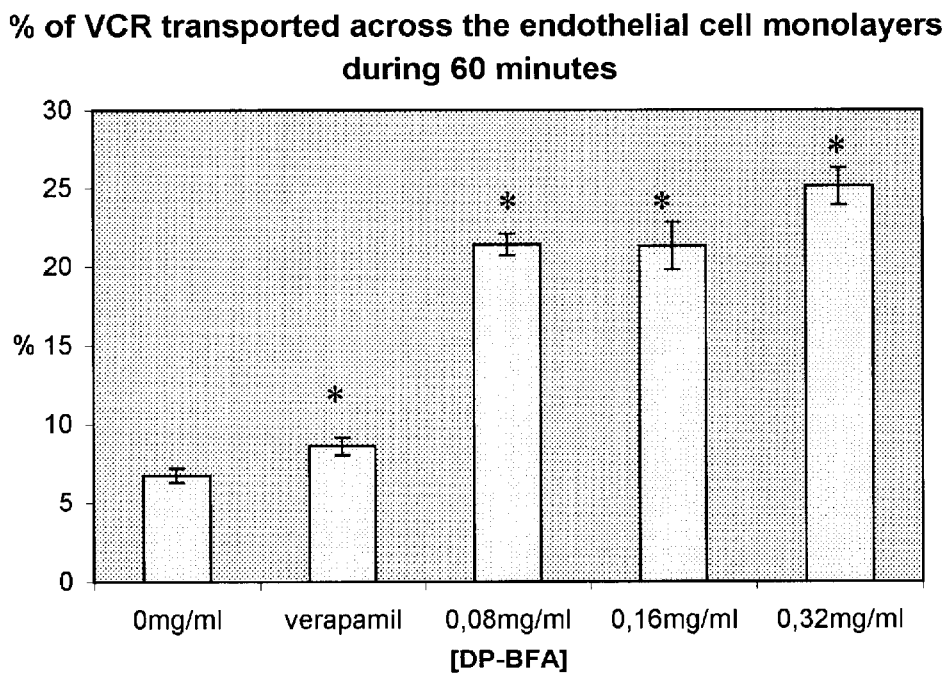
FIG. 3 depicts the percentage of vincristine transported across the endothelial cell monolayers following 60 min. incubation in the presence of verapamil, 0.08 mg/ml, 0.16 mg/ml or 0.32 mg/ml DP-BFA as indicated in the figure. *-denotes significant measurements over the control of endothelial cells in the presence of vincristine+sucrose only.
Figure 4:
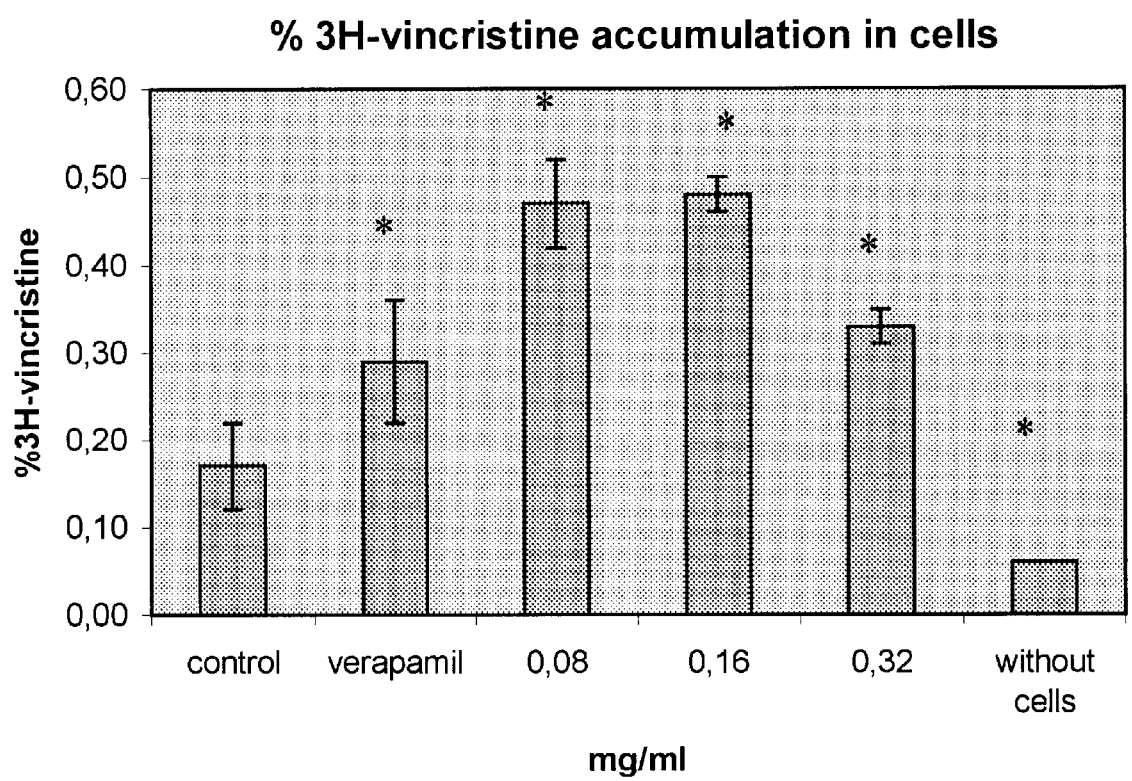
FIG. 4 depicts vincristine accumulation in endothelial cells in the presence of verapamil, 0.08 mg/ml, 0.16 mg/ml or 0.32 mg/ml DP-BFA as indicated in the figure. *-denotes significant measurements over the control of endothelial cells in the presence of vincristine+sucrose only.

The effects of verapamil and the different concentrations of DP-3,14 on vincristine transport across the endothelial cell monolayers and vincristine accumulation in the cells are shown in FIGS. 2, 3 and FIG. 4, respectively, and are summarized below:

1) Permeability coefficients for $[^{14}C]$-sucrose measured on endothelial cells incubated in HEPES-buffered Ringer solution containing or not, 50 nM vincristine or 50 nM vincristine+verapamil 25 µM, were not significantly different ($Pe_{sucrose}=1.16\pm0.05\times10^{-3}$ cm/min without vincristine and verapamil; $Pe_{sucrose}=1.33\pm0.08\times10^{-3}$ cm/min with vincristine; $Pe_{sucrose}=1.26\pm0.08\times10^{-3}$ cm/min with vincristine and verapamil). These results indicate that vincristine and verapamil were not toxic for the endothelial cells and the integrity of the monolayers was preserved.

2) A 1.3-fold increase in the transport of vincristine was demonstrated in the endothelial cells incubated with vincristine±verapamil (%=6.76±0.44 without verapamil; %=8.58±0.54 with verapamil).

3) A significant clearance of vincristine (FIG. 2) was observed in the presence of DP-3,14, even with the lowest concentration used, i.e. 0.08 mg/ml. However, these values were similar to the vincristine clearance of the control without cells. The results concur with the demonstrated effect of 0.08, 0.16 and 0.32 mg/ml DP-3,14 in significantly increasing the sucrose permeability of the monolayer (respectively, 274%, 266% and 278%, measured at 60 min.).

4) Cellular accumulation of vincristine, measured after 60 min. incubation in the presence of DP-3,14, was significantly increased, and at least with 0.08 and 0.16 mg/ml DP-3,14 was more pronounced than the same effect induced by verapamil (FIG. 4).

Conclusion:

An increase in the transport of vincristine could be observed when the endothelial cells were incubated in the presence DP-3,14 (0.08, 0.16 and 0.32 mg/ml), which increase was greater than that with verapamil (FIG. 3).

Example 5

Effect of Low Concentrations of DP-BFA on P-Glycoprotein

In order to determine if DP-BFA can inhibit P-glycoprotein, similar experiments as described above were performed using lower concentrations of DP-3,14, which do not open the tight junctions of the BBB.

The permeability of the monolayer of endothelial cells was studied in the in vitro model system of the BBB, using the same procedures described above in Example 4, except that lower concentrations of DP-3,14, i.e. 0.001, 0.005, 0.01, 0.02 and 0.08 mg/ml were employed.

Figure 5A:
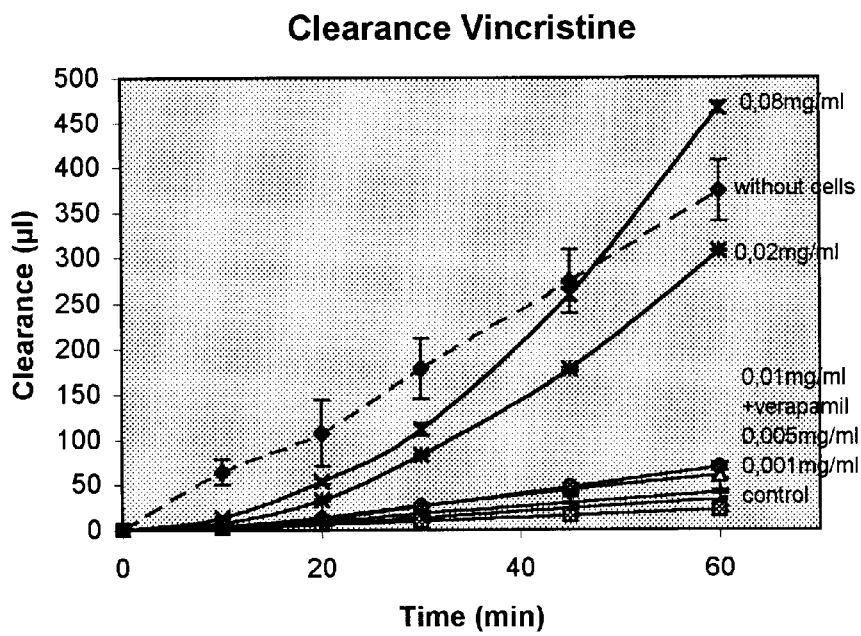
FIGS. 5A–B depict clearance of [$^3$H]-vincristine in the in vitro model system of BBB, as a function of incubation time with either verapamil, 0.001 mg/ml, 0.005 mg/ml, 0.01 mg/ml, 0.02 mg/ml or 0.08 mg/ml DP-BFA. As controls serve the clearances of vincristine through filters with and without endothelial cells in the presence of [$^3$H]-vincristine+ $^{14}$C-sucrose only (marked as "control" and "without cells", respectively).
Figure 5B:
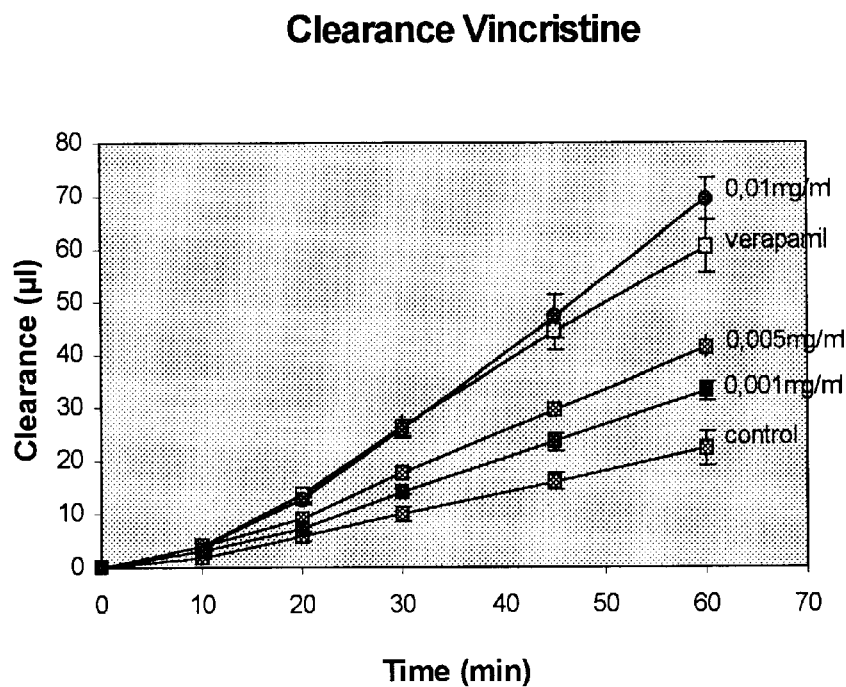
Figure 6A:
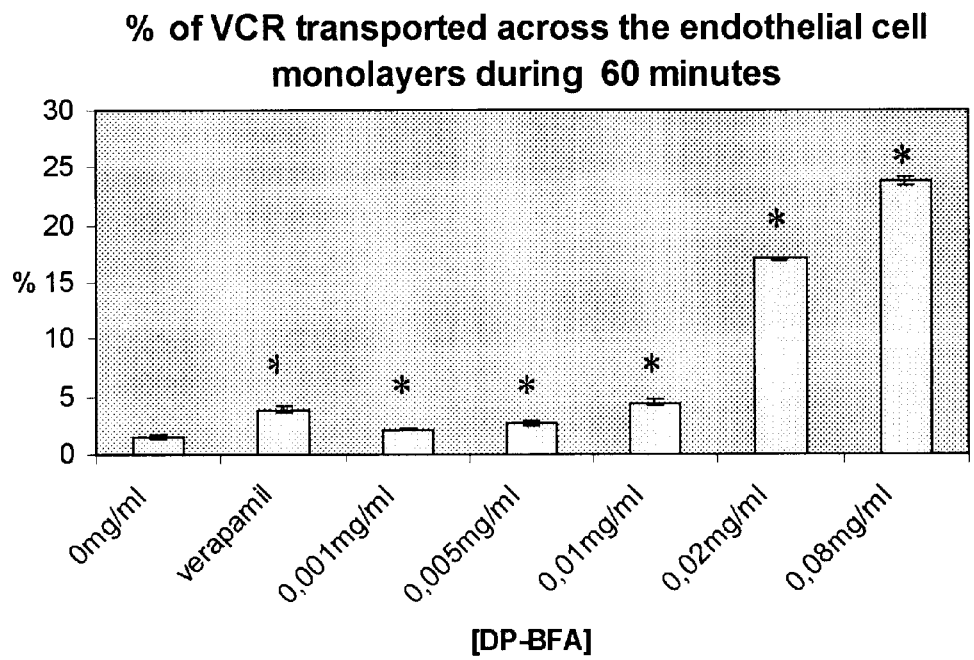
FIGS. 6A–B depict the percentage of vincristine transported across the endothelial cell monolayers following 60 min. incubation in the presence of verapamil, 0.001 mg/ml, 0.005 mg/ml, 0.01 mg/ml, 0.02 mg/ml or 0.08 mg/ml DP-BFA as indicated in the figure. *-denotes significant measurements over the control of endothelial cells in the presence of vincristine+sucrose only.
Figure 6B:
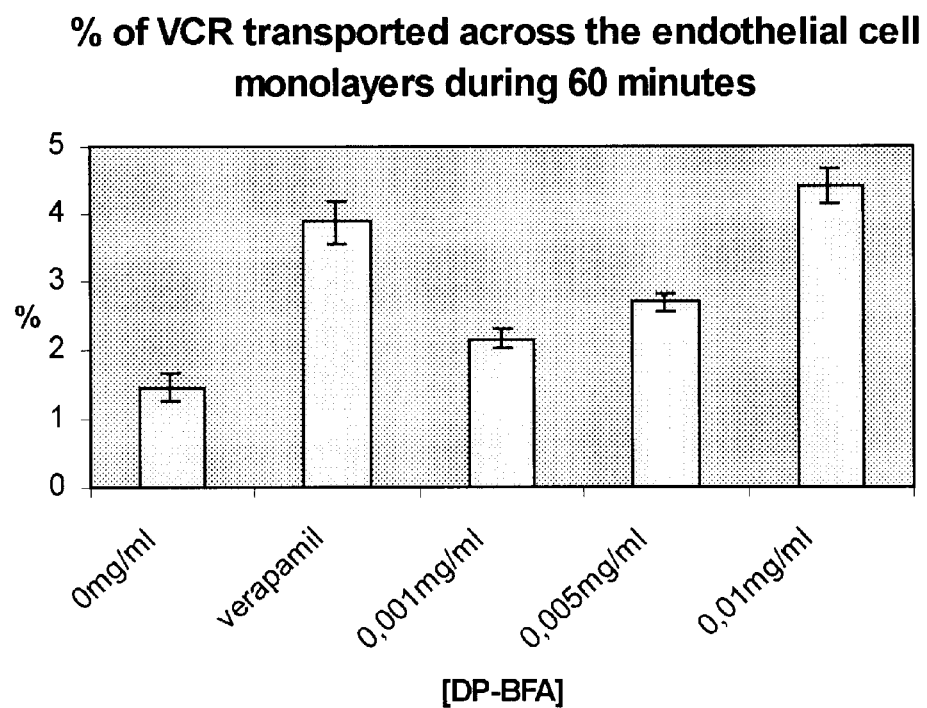
Figure 7:
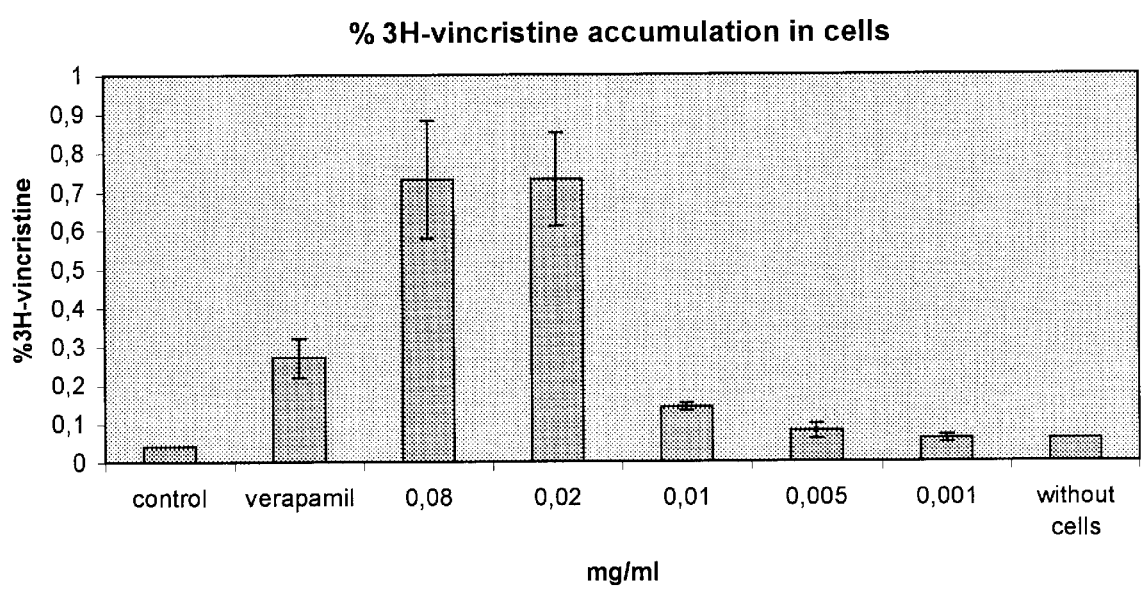
FIG. 7 depicts vincristine accumulation in endothelial cells in the presence of verapamil, 0.08 mg/ml, 0.02 mg/ml, 0.01 mg/ml, 0.005 mg/ml or 0.001 mg/ml DP-BFA as indicated in the figure.

The results of this set of experiments are shown in FIGS. 5, 6 and 7 and are summarized below:

1) A 2.7-fold increase in the transport of vincristine was demonstrated in the endothelial cells incubated with vincristine±verapamil (%=1.46±0.21 without verapamil; %=3.88±0.32 with verapamil).
2) A significant increase in the transport of vincristine was observed already with the lowest concentration of DP-3, 14 used, i.e. 0.001 mg/ml. Larger effects were detected with the higher concentrations 0.02 and 0.08 mg/ml (FIGS. 5 and 6).
3) Significant increases in the sucrose permeability of the monolayer (452% and 574%, measured at 60 min.) were measured in the presence of the two higher concentrations of DP-3,14 employed, i.e. 0.02 and 0.08 mg/ml. At two lower concentrations, 0.001 and 0.005 mg/ml, a significant decrease in the sucrose permeability of the monolayer was measured (respectively, 66% and 68%). No change in sucrose permeability was observed with 0.01 mg/ml DP-3,14. It can be concluded that in contrast to the higher concentrations of the DP-3,14, the lower concentrations examined, did not impair the integrity of the endothelial cell monolayer.
4) A 60 minute incubation of endothelial cells with vincristine in the presence of 0.02 or 0.08 mg/ml DP-3,14, resulted in an increase in vincristine uptake. The drug accumulation in the cells in these cases was 2–3 fold higher than that caused by verapamil. When the same experiment was performed with 0.001, 0.005 or 0.01 mg/ml DP-3,14, an increase in vincristine uptake was lower than that observed with verapamil (FIG. 7).

Conclusion:

An increase in the transport of vincristine was demonstrated in the presence of low concentration (0.001—0.01 mg/ml) of DP-3,14. At these concentrations, no increase in the transport of sucrose (the paracellular marker) occurs. Therefore, the increase in the vincristine uptake is not due to the opening of the tight junctions of the BBB, but rather is attributed to the branched chain fatty acid's inhibition of P-glycoprotein.

Furthermore, no paracellular breakdown (opening of the tight junctions) of endothelial cells was noted with 0.01 mg/ml DP-3,14, even after 48 hours incubation.

Example 6

Effect of DP-BFA on Drug-resistant Cells With Elevated Levels of P-Glycoprotein

The effect of DP-BFAs in inhibition of P-glycoprotein (P-gp) was demonstrated in vitro in cultured cell lines which are multidrug resistant due to increased activity of P-gp.

The cell line employed was the human uterine sarcoma cell line MES-SA/Dx5 (ATCC number CRL-1977), which is a multiple drug resistant cell line that expresses high levels of P-glycoprotein. The effect of DP-BFA in enhancing the cytotoxic activity of the anti-cancer drug, doxorubicin, was measured.

MES-SA/Dx5 cells were seeded in 96 well plates at a density of $5 \times 10^4$ cells/ml in 90% McCoy's 5a medium plus 10% fetal calf serum. The cultured cells were incubated, during their linear growth phase with 125 ng/ml doxorubicin, in the absence and presence of DP-BFAs at concentrations ranging from 1 to 100 μg/ml. After 72 hours incubation at 37° C. the anti-proliferative effect on the cells was estimated by using the colorimetric MTT assay (Mosmann (1983) J. Immunol Methods 65: 55–63) that measures mitochondrial reductase activity and serves for quantitative assessment of cellular viability.

In a calibration set of experiments it was found that MES-SA/Dx5 cells are resistant to doxorubicin up to a concentration of 250 ng/ml. The non-toxic concentrations of the DP-BFAs, under the experimental conditions employed, were determined to be lower than 100 μMolar, which is the equivalent of 20 to 30 μg/ml of the tested DP-BFAs mentioned below. Plates wherein MES-SA/Dx5 cells were incubated with sub-toxic concentrations of doxorubicin (125 ng/ml) and of verapamil (<12.5 1 μg/ml), served as a positive control for demonstrating the inhibitory effect of verapamil on P-gp.

The tested DP-BFAs were as follows:
2-heptylnonanoic acid (DP-7,7)
2-propyldodecanoic acid (DP-3,10)
2, 3-propynyltetradecanoic acid (DP-3-yl, 12)

Results of the experiment using sub-toxic concentrations of DP-BFAs are shown in Table 1.

TABLE 1

Effect of DP-BFA on toxicity of doxorubicin (dox) in multi-drug resistant cells (MES-SA/Dx5)

| Compound | | % Toxicity |
|---|---|---|
| Dox | (0.125 μg/ml) | 0 |
| Verapamil | (3.125 μg/ml) | 0.1 |
| Dox + Verapamil | (3.125 μg/ml) | 34 |
| Verapamil | (6.25 μg/ml) | 0.99 |
| Dox + Verapamil | (6.25 μg/ml) | 46 |
| DP-7,7 | (3.125 μg/ml) | 0.1 |
| Dox + DP-7,7 | (3.125 μg/ml) | 9.9 |
| DP-3-yl,12 | (3.125 μg/ml) | 0.48 |
| Dox + DP-3-yl,12 | (3.125 μg/ml) | 4.8 |
| DP-3,10 | (12.5 μg/ml) | 0.1 |
| Dox + DP-3,10 | (12.5 μg/ml) | 17.4 |

As can be seen from the results in Table 1, sub-toxic concentrations of the tested DP-BFAs compounds increased the sensitivity of the multi-drug resistant cell line to doxorubicin. The results indicate that the MDR phenotype is at least partially overcome by the addition of DP-BFA, and support the finding that DP-BFAs are effective in inhibiting P-gp.

Example 7

Effect of DP-BFA on MDR Tumor Growth (in vivo study)

The beneficial effect of DP-BFAs in inhibiting P-gp and hence overcoming MDR phenotype may further be demonstrated in vivo in an animal model system. For this purpose, a model system of MDR-tumor-bearing mice is used.

DBA2 mice (20–30 gr.) are subcutaneously (s.c.) injected into the dorsal side with $10^5$ to $10^6$ T19 tumor cells (provided by Dr. Y. Assaraf, Technion Institute of Technology, Israel). T19 is a cell line derived from the Chinese hamster ovary (CHO) parent cell line AA8, which has been characterized as having anti-cancer drug resistance due to over-expression of P-gp. Tumors of measurable size, i.e. tumors of around 5 mm in diameter, are developed in about 10 to 14 days following the inoculation of the tumor cells.

The mice in the experiment are randomly assigned into 4 groups, each group is treated with different compositions while using the same regimen and means of administration. Treatments start on the second day following inoculation and include administration of the tested composition every two days for a period of 60 days.

Group 1- tumor-bearing rats treated with vehicle solution (control, untreated).

Group 2- tumor-bearing rats treated with an anti-cancer agent.

Group 3- tumor-bearing rats treated with DP-BFA.

Group 4- tumor-bearing rats treated with the anti-cancer agent in combination with DP-BFA.

Appropriate anti-cancer agents for use in this experiment are those which are effective cytotoxic agents in the AA8 parent cell line and in addition are drugs that are known to be subjected to P-gp action. For example, the tumors may be challenged with doxorubicin, Taxol, vincristine or combinations thereof. The cytotoxic drug(s) may be orally, intraperitonealy (i.p.), intravenously (i.v.) or subcutaneously (s.c.) administered.

The animals are monitored on a daily basis for viability and signs of morbidity (e.g. rough coat, heavy breathing and nervousness). The tumor volume is determined based on measurements of the tumor diameters taken every other day using a caliber device.

The formula for tumor volume calculation is as follows.

Volume (in mm$^3$)=length×width$^2$×0.5

Efficacy of each of the tested DP-BFA compounds in enhancing the anti-tumor activity of the employed anti-cancer agent is assessed by comparison of the tumor size in the animals treated with the cytotoxic drug in the absence and presence of DP-BFA. Under these experimental conditions, untreated mice implanted with tumors usually die within about 15 to 30 days following inoculation of the tumor cells. Treatments with the anti-cancer agent or DP-BFA by themselves have a very little anti-tumor effect, if at all. On the other hand, treatment with the combination of the anti-cancer agent and DP-BFA (Group 4) improves the condition of the tumor-bearing animals, increases survival or effectively prolongs animals life span.

It is suggested that DP-BFAs effect in improving the anti-cancer activity of the tested drug and in counteracting the MDR phenotype is by inhibition of the P-gp activity.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. A method for inhibiting the activity of P-glycoprotein comprising contacting cells having P-glycoprotein with an effective amount of a compound of the general formula I:

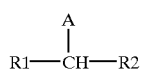
(I)

Wherein

R1 is a saturated or unsaturated, substituted or unsubstituted hydrocarbon chain having from 1 to 10 carbon atoms;

R2 is a saturated or unsaturated, substituted or unsubstituted hydrocarbon chain having from 5 to 30 carbon atoms;

A is selected from the group consisting of C(O)OH, C(O)O—R', C(O)NH$_2$, C(O)NH—R', and C(O)O$^-$Y$^+$, wherein R' is a lower alkyl group comprising 1–5 carbon atoms, and Y denotes any pharmaceutically acceptable counter-ion.

2. The method according to claim 1, wherein said compound of the general formula I is selected from the group consisting of:

2-propylnonanoic acid,
2-propyldodecanoic acid,
2-propyltetradecanoic acid,
2-propylhexadecanoic acid,
2-propyloctadecanoic acid,
2-propyleicosanoic acid,
2-heptylnonanoic acid,
2-heptyldodecanoic acid,
2-heptylhexadecanoic acid,
2-decyldodecanoic acid,
2-decylhexadecanoic acid,
2-tetradecylhexadecanoic acid,
2,3-propynyltetradecanoic acid,
2,3-propynylhexadecanoic acid,
2-propylnonanoylamide,
2-propyldecanoylamide,
2-propyltetradecanoylamide,
2-propylhexadecanoylamide,
2-propyloctadecanoylamide, and
2-propyleicosanoylamide.

3. A method for treatment of a tumor associated with increased activity of P-glycoprotein comprising administering to a patient in need thereof an effective amount of a compound of the following general formula I in combination with an anti-cancer drug, whereby cells of said tumor having P-glycoprotein are contacted with said compound of the following general formula I,

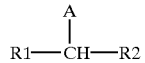
(I)

wherein

R1 is a saturated or unsaturated, substituted or unsubstituted hydrocarbon chain having from 1 to 10 carbon atoms;

R2 is a saturated or unsaturated, substituted or unsubstituted hydrocarbon chain having from 5 to 30 carbon atoms;

A is selected from the group consisting of C(O)OH, C(O)O—R', C(O)NH$_2$, C(O)NH—R', and C(O)O$^-$Y$^+$, wherein R' is a lower alkyl group comprising 1–5 carbon atoms, and Y denotes any pharmaceutically acceptable counter-ion.

4. The method according to claim 3, wherein said anti-cancer drug is administered in a separate pharmaceutical composition.

5. The method according to claim 3, wherein said tumor associated with said increased activity of P-glycoprotein is a multi-drug resistant tumor.

6. The method according to claim 3, wherein said tumor associated with said increased activity of P-glycoprotein is selected from the group consisting of carcinomas, sarcomas, leukemias, lymphomas, myelomas and gliomas.

7. The method according to claim 3, wherein said anticancer drug is selected from the group consisting of taxol, vinblastine, vindesine, vincristine, cyclophosphamide, aclacinomycin, actinomycin, anthramycin, daunorubicin, doxorubicin, raltitrexed, carboplatin, cisplatin, miboplatin and oxaliplatin.

8. The method according to claim 3, wherein said compound of the general formula I is orally administered.

9. The method according to claim 3, wherein said compound of the general formula I is intravenously administered.

10. A method for administration of diagnostic agents into cells associated with increased activity of P-glycoprotein comprising contacting said cell having P-glycoprotein with a diagnostic agent in the presence of an effective amount of a compound of the following general formula I, thus enabling or increasing the penetration and/or accumulation of the diagnostic agent in the cells,

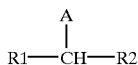

(I)

wherein

R1 is a saturated or unsaturated, substituted or unsubstituted hydrocarbon chain having from 1 to 10 carbon atoms;

R2 is a saturated or unsaturated, substituted or unsubstituted hydrocarbon chain having from 5 to 30 carbon atoms;

A is selected from the group consisting of C(O)OH, C(O)O—R', C(O)NH$_2$, C(O)NH—R', and C(O)O$^-$Y$^+$, wherein R' is a lower alkyl group comprising 1–5 carbon atoms, and Y denotes any pharmaceutically acceptable counter-ion.

11. A method for increasing accumulation of a diagnostic agent in an organ protected by a biological barrier comprising administering to an individual said diagnostic agent in combination with an effective amount of a compound of the following general formula I, whereby cells of said biological barrier having P-glycoprotein are contacted with said compound of the following general formula I, thus increasing accumulation of the diagnostic agent in the organ protected by a biological barrier,

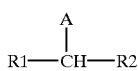

(I)

wherein

R1 is a saturated or unsaturated, substituted or unsubstituted hydrocarbon chain having from 1 to 10 carbon atoms;

R2 is a saturated or unsaturated, substituted or unsubstituted hydrocarbon chain having from 5 to 30 carbon atoms;

A is selected from the group consisting of C(O)OH, C(O)O—R', C(O)NNH$_2$, C(O)NH—R', and C(O)O$^-$Y$^+$, wherein R' is a lower alkyl group comprising 1–5 carbon atoms, and Y denotes any pharmaceutically acceptable counter-ion.

12. The method according to claim 11, wherein said organ protected by the biological barrier is brain, eye, testis or prostate gland.

13. A method for administration of a biologically active molecule into cells associated with increased activity of P-glycoprotein comprising contacting said cells having P-glycoprotein with said biologically active molecule in the presence of an effective amount of a compound of the following general formula I, thus enabling or increasing the penetration and/or accumulation of the biologically active molecule in the cells,

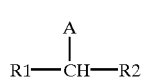

(I)

wherein

R1 is a saturated or unsaturated, substituted or unsubstituted hydrocarbon chain having from 1 to 10 carbon atoms;

R2 is a saturated or unsaturated, substituted or unsubstituted hydrocarbon chain having from 5 to 30 carbon atoms;

A is selected from the group consisting of C(O)OH, C(O)O—R',C(O)NH$_2$, C(O)NH—R', and C(O)O$^-$Y$^+$, wherein R' is a lower alkyl group comprising 1–5 carbon atoms, and Y denotes any pharmaceutically acceptable counter-ion.

14. A method for increasing accumulation of biologically active molecules in an organ protected by a biological barrier comprising administering to an individual a biologically active molecule in combination with an effective amount of a compound of the following general formula I, whereby cells of said biological barrier having P-glycoprotein are contacted with said compound of the following general formula I, thus increasing accumulation of the biologically active molecule in the organ protected by a biological barrier,

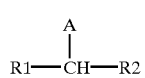

(I)

wherein

R1 is a saturated or unsaturated, substituted or unsubstituted hydrocarbon chain having from 1 to 10 carbon atoms;

R2 is a saturated or unsaturated, substituted or unsubstituted hydrocarbon chain having from 5 to 30 carbon atoms;

A is selected from the group consisting of C(O)OH, C(O)O—R', C(O)NHI2, C(O)NH—R', and C(O)O$^-$Y$^+$, wherein R' is a lower alkyl group comprising 1–5 carbon atoms, and Y denotes any pharmaceutically acceptable counter-ion.

15. The method according to claim 14, wherein said organ protected by the biological barrier is brain, eye, testis or prostate gland.

16. A method for increasing bioavailability of a drug comprising administering to an individual said drug in combination with an effective amount of a compound of the following general formula I, whereby cells in said individual having P-glycoprotein are contacted with said compound of the following general formula I,

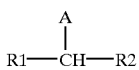 (I)

wherein
- R1 is a saturated or unsaturated, substituted ox unsubstituted hydrocarbon chain having from 1 to 10 carbon atoms;
- R2 is a saturated or unsaturated, substituted or unsubstituted hydrocarbon chain having from 5 to 30 carbon atoms;
- A is selected from the group consisting of C(O)OH, C(O)O—R', C(O)NH$_2$, C(O)NH—R', and C(O)O$^-$Y$^+$, wherein R' is a lower alkyl group comprising 1–5 carbon atoms, and Y denotes any pharmaceutically acceptable counter-ion.

17. The method according to claim 16 wherein said drug is orally, nasally or parenterally administered.

18. A method for increasing drug absorption through a biological barrier comprising administering to an individual a drug in combination with an effective amount of a compound of the following general formula I, whereby cells of said biological barrier having P-glycoprotein are contacted with said compound of the following general formula I, thus increasing the drug absorption through said biological barrier,

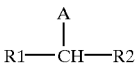 (I)

wherein
- R1 is a saturated or unsaturated, substituted or unsubstituted hydrocarbon chain having from 1 to 10 carbon atoms;
- R2 is a saturated or unsaturated, substituted or unsubstituted hydrocarbon chain having from 5 to 30 carbon atoms;
- A is selected from the group consisting of C(O)OH, C(O)O—R', C(O)NH$_2$, C(O)NH—R', and C(O)O$^-$Y$^+$, wherein R' is a lower alkyl group comprising 1–5 carbon atoms, and Y denotes any pharmaceutically acceptable counter-ion.

19. The method according to claim 18 wherein said biological barrier is selected from the group consisting of the gastrointestinal epithelium, epithelia of the nasal cavity, epithelia of the bronchi and renal epithelia.

* * * * *